United States Patent [19]

Jaquess

[11] Patent Number: 5,356,800
[45] Date of Patent: Oct. 18, 1994

[54] STABILIZED LIQUID ENZYMATIC COMPOSITIONS

[75] Inventor: Percy A. Jaquess, Tigrett, Tenn.

[73] Assignee: Buckman Laboratories International, Inc., Memphis, Tenn.

[21] Appl. No.: 983,360

[22] Filed: Nov. 30, 1992

[51] Int. Cl.$^5$ .......................... C12N 9/96; C11D 1/18
[52] U.S. Cl. .................................. 435/188; 252/546; 252/545; 252/DIG. 12
[58] Field of Search ................. 435/188; 252/546, 545, 252/DIG. 12

[56] References Cited

U.S. PATENT DOCUMENTS

| | | | |
|---|---|---|---|
| 3,627,688 | 12/1971 | McCarty et al. | 435/188 |
| 3,773,674 | 11/1973 | Adam et al. | 435/188 |
| 3,819,528 | 6/1974 | Berry | 435/188 |
| 3,901,666 | 8/1975 | Rosenwald | 44/72 |
| 4,142,999 | 3/1979 | Bloching et al. | 252/544 |
| 4,169,817 | 10/1979 | Weber | 252/545 |
| 4,243,543 | 1/1981 | Guilbert et al. | 252/105 |
| 4,313,895 | 2/1982 | Richmond et al. | 260/501.15 |
| 4,318,818 | 3/1992 | Letton et al. | 252/174.12 |
| 4,419,140 | 12/1983 | Richmond et al. | 106/273 N |
| 4,462,922 | 7/1984 | Boskamp | 435/188 |
| 4,491,642 | 1/1985 | Atkins | 523/515 |
| 4,548,727 | 10/1985 | Shaer | 252/171 |
| 4,555,534 | 11/1985 | Atkins | 523/507 |
| 4,801,544 | 1/1989 | Munk | 435/188 |
| 4,810,413 | 3/1989 | Pancheri et al. | 252/174.12 |
| 4,906,396 | 3/1990 | Falholt et al. | 435/188 |
| 4,912,056 | 3/1990 | Olson | 435/188 |
| 4,936,994 | 6/1990 | Wiatr | 210/632 |
| 5,198,353 | 3/1993 | Hawkins et al. | 435/188 |

FOREIGN PATENT DOCUMENTS 0352244  1/1990  European Pat. Off. .
2169752  9/1973  France .

OTHER PUBLICATIONS

R. Schmid, Stabilized Soluble Enzymes. Part 3, Enzyme Stabilization, 10211 Adv. Biochem. Eng. 12:55-67 (1979).

McCutcheon's, Emulsifiers & Detergents, 1982, pp. 295 & 224.
McCutcheon's Emulsifiers and Detergents 1982 Edition pp. 44, 59.
Dr. Ow, World Pulp and Paper Technology, 1992.
VAI-BIO Bleaching, Technical Disclosure.
Roberta L. Farrell, Repligen Sandoz Research Corporation.
David J. Senior et al., Manuscript CPPA Environmental Conference, 1991.

(List continued on next page.)

Primary Examiner—David M. Naff
Assistant Examiner—Michael V. Meller
Attorney, Agent, or Firm—Finnegan, Henderson, Farabow, Garrett & Dunner

[57] ABSTRACT

A stabilizing formulation capable of enhancing the storage and shelf-life of liquid enzymatic compositions as well as acting as a dispersant aid for industrial process waters. Such stabilizing formulation contains at least one water-soluble coupling agent selected from a short chain alcohol and a short chain glycol, at least one of (i) a polyethoxylated alkyl diamine and (ii) an amine oxide, and water. The polyethoxylated alkyl diamine and/or amine oxide is present in an amount effective to stabilize one or more enzymes contained in a liquid enzymatic composition. A stabilized liquid enzymatic composition may contain one or more components of the stabilizing formulation and an enzyme. Methods for the stabilization of a liquid enzymatic composition which involve the step of adding one or more enzymes to a stabilizing formulation, or the step of combining a stabilizing formulation with a liquid enzymatic composition containing one or more enzymes where the diamine and/or amine oxide is present, after addition, in an amount effective to stabilize one or more of the enzymes.

49 Claims, No Drawings

OTHER PUBLICATIONS

Neils Munk, Enzyme Process Division, R&D.

Chemical Marketing Reporter, Dec. 30, 1991.

Kurt Fischer et al., Tappi Journal, Feb. 1992, pp. 130–134.

Technical Literature Search Conducted by Applicants.

Prasad et al., Progress in Paper Recycling, May 1992, pp. 21–30.

Technical Literature, Novo Nordisk.

Product Disclosure, Novo Nordisk.

David J. Senior et al., Manuscript, 1991 International Pulp Bleaching Conference Stockhelm, CPPA Environmental Conference, Quebec.

R. Koponen Article Biotechnology.

Thomas W. Jeffries, Materials and Chemicals from Biomass, American Chemical Society, Wash. D.C., 1992, pp. 313–329.

Jurgen Christner, JALCA, vol. 87, 1992, pp. 129–139.

Far Eastern Economic Review, Oct. 22, 1992.

Paper, Jun. 1992.

Encyclopedia of Chemical Technology, vol. 2 Alkanolamines pp., 357–357, vol. 9, Enzymes, Industrial, pp. 199, 200, 202.

Technology Article.

STABILIZED LIQUID ENZYMATIC COMPOSITIONS

The present invention relates to novel formulations for stabilizing one or more enzymes contained in liquid enzymatic compositions. These stabilizing formulations can enhance the storage and shelf-life of liquid enzymatic compositions, even at high and low temperatures. The invention also relates to stabilized liquid enzymatic compositions. Additionally, the invention relates to novel methods for the stabilization of liquid enzymatic compositions.

The use of enzymes and liquid enzymatic compositions in industry and in the commercial marketplace has grown rapidly over the last several years, As is well-known, enzymes can be acid, alkaline or neutral, depending upon the pH range in which they are active. All of these types of enzymes are contemplated to be useful in connection with the invention disclosed herein.

Many enzymes and liquid enzymatic compositions have been associated with liquid detergents and have shown utility as solubilizing and cleaning formulations. In addition to their association with liquid detergents, enzymes and liquid enzymatic compositions have also shown utility in a number of different commercial and industrial areas in which a wide variety of enzyme classes are now used.

Proteases are a well-known class of enzymes frequently utilized in a wide variety of industrial applications where they act to hydrolyze peptide bonds in proteins and proteinaceous substrates. Commercially, the greatest uses of proteases are made in the laundry detergent industry, where they help to remove protein based stains such as blood or egg stains, and in the cheesemaking industry, where they aid in curdling milk. Proteases are also used as meat tenderizers, for softening leather, for modifying food ingredients, and for flavor development. Liquid enzymatic compositions containing alkaline proteases have also shown to be useful as dispersants of bacterial films and algal and fungal mats in cooling tower waters and metalworking fluid containment bays.

Proteases can be characterized as acid, neutral, or alkaline proteases depending upon the pH range in which they are active. The acid proteases include the microbial rennets, rennin (chymosin), pepsin, and fungal acid proteases. The neutral proteases include trypsin, papain, bromelain/ficin, and bacterial neutral protease. The alkaline proteases include subtilisin and related proteases. Commercial liquid enzymatic compositions containing proteases are available under the names Rennilase®, "PTN" (Pancreatic Trypsin NOVO), "PEM" (Proteolytic Enzyme Mixture), Neutrase®, Alcalase®, Esperase®, and Savinase™ which are all supplied by Novo Nordisk Bioindustrials, Inc. of Danbury, Conn. Another commercial protease is available under the name HT-Proteolytic supplied by Solvay Enzyme Products.

Amylases, another class of enzymes, have also been utilized in many industrial and commercial processes in which they act to catalyze or accelerate the hydrolysis of starch. Amylases are used largely in the corn syrup industry for the production of glucose syrups, maltose syrups, and a variety of other more refined end products of starch hydrolysis such as high fructose syrups. As a class they include α-amylase, β-amylase, amyloglucosidase (glucoamylase), fungal amylase, and pullulanase. Commercial liquid enzymatic compositions containing amylases are available under the names BAN, Termamyl®, AMG, Fungamyl®, and Promozyme™, which are supplied by Novo Nordisk, and Diazyme L-200, a product of Solvay Enzyme Products.

Other commercially valuable enzyme classes are those which affect the hydrolysis of fiber. These classes include cellulases, hemicellulases, pectinases, and β-glucanases. Cellulases are enzymes that degrade cellulose, a linear glucose polymer occurring in the cell walls of plants. Hemicellulases are involved in the hydrolysis of hemicellulose which, like cellulose, is a polysaccharide found in plants. The pectinases are enzymes involved in the degradation of pectin, a carbohydrate whose main component is a sugar acid. β-glucanases are enzymes involved in the hydrolysis of β-glucans which are also similar to cellulose in that they are linear polymers of glucose. In a commercial context, these enzymes have utility to a greater or lesser degree in manufacturing processes dependent on fiber degradation.

Cellulases have reported utility in the de-inking process of old newsprint (ONP) wastepaper, eliminating the need for any surfactants and alkaline chemicals. The enzymes dislodge inks from fiber surfaces and disperse ink particles to a finite size. See S. Say-Kyoun Ow, *Biological De-Inking Methods of Newsprint Wastepaper*, World Pulp and Paper Technology, pp. 63, 64 (1992). Collectively, cellulases include endocellulase, exocellulase, exocello-biohydrolase, and celloblase. Commercial liquid enzymatic compositions containing cellulases are available under the names Celluclast® and Novozym®188 which are both supplied by Novo Nordisk.

Hemicellulases are also used in the de-inking process to dislodge ink particles from the fiber surface of ONP. See D. Y. Prasad et al., *Enzyme Deinking of Black and White Letterpress Printed Newsprint Waste*, Progress in Paper Recycling, May 1992, pp. 21, 22. Additionally, hemicellulases, such as the xylanases, are employed in the pulp bleaching process. Xylanase pretreatment of kraft pulps has resulted in major reductions in bleaching chemical requirements, such as molecular chlorine, and has also improved pulp quality as reflected by higher brightness ceilings. See D. J. Senior etal., *Reduction in Chlorine Use During Bleaching of Kraft Pulp Following Xylanase Treatment*, Tappi Journal (forthcoming publication; aspects of the publication were presented at the 1991 International Pulp Bleaching Conference, Stockholm). PULPZYM® product, available from Novo Nordisk, and ECOPULP® product, from Alko Biotechnology, are two examples of commercially available liquid enzymatic compositions containing xylanase-based bleaching enzymes.

As a class, hemicellulases include hemicellulase mixture and galactomannanase. Commercial liquid enzymatic compositions containing hemicellulases are available as PULPZYM® from Novo, ECOPULP® from Alko Biotechnology and Novozym®280 and Gamanase™, which are both products of Novo Nordisk.

The pectinases are used commercially to weaken cell walls and enhance extraction of fruit juice, as well as to aid in decreasing viscosity and preventing gelation in these extracts. Pectinases consist of endopolygalacturonase, exopolygalacturonase, endopectate lyase (transeliminase), exopectate lyase (transeliminase), and endopectin lyase (transeliminase). Commercial liquid enzymatic compositions containing pectinases are available under the names Pectinex ™ Ultra SP and Pectinex ™ *, both supplied by Novo Nordisk.

The β-glucanases are of importance in malting and brewing industries where modification of barley cell walls containing β-glucans is necessary. β-glucanases are comprised of lichenase, laminarinase, and exoglucanase. Commercial liquid enzymatic compositions containing β-glucanases are available under the names Novozym ®234, Cereflo ®, BAN, Finizym ®, and Ceremix ®, all of which are supplied by Novo Nordisk.

Two additional classes of industrially and commercially useful enzymes are lipases and phospholipases. Lipases and phospholipases are esterase enzymes which hydrolyze fats and oils by attacking the ester bonds in these compounds. Lipases act on triglycerides, while phospholipases act on phospholipids. In the industrial sector, lipases and phospholipases represent the commercially available esterases, and both currently have a number of industrial and commercial applications.

In the pulp and paper industry, liquid enzyme preparations containing lipases have proven to be particularly useful in reducing pitch deposits on rolls and other equipment during the production process. For example, the treatment of unbleached sulfite pulp with lipases prior to bleaching with chlorine to reduce the content of chlorinated triglycerides, which are reportedly the cause of pitch deposition during the paper manufacturing process, has been reported. See K. Fischer and K. Messher, *Reducing Troublesome Pitch in Pulp Mills By Lipolytic Enzymes,* Tappi Journal, Feb. 1992, p. 130. Novo Nordisk markets two liquid enzyme preparations under the names Resinase ™ A and Resinase ™ A 2X, both of which, under certain conditions, reportedly reduce pitch deposits significantly by breaking down wood resins in pulp.

Another important use of lipases is to degrease hides and pelts in the leathermaking process. Alkaline lipases are used in conjunction with special proteases and emulsifying systems to aid degreasing, as well as to improve the soaking and liming effect in leathermaking. See J. Christher, *The Use of Lipases in the Beamhouse Processes,* 87 J.A.L.C.A. 128 (1992).

Lipases have also been used for the development of flavors in cheese and to improve the palatability of beef tallow to dogs. In nonaqueous systems, lipases have been employed to synthesize esters from carboxylic acids and alcohols.

Commercial liquid enzymatic compositions containing lipases are available under the names Lipolase 100, Greasex 50L, Palatase ™ A, Palatase ™ M, and nipozyme ™ which are all supplied by Novo Nordisk.

With respect to the commercially useful phospholipases, pancreatic phospholipase $A_2$ has been used to convert lecithin into lysolecithin. Lysolecithin reportedly is an excellent emulsifier in the production of mayonnaise and the baking of bread. Commercially, phospholipase $A_2$ is available in a liquid enzymatic composition sold as LECITASE ™ by Novo Nordisk.

Another commercially valuable class of enzymes are the isomerases which catalyze conversion reactions between isomers of organic compounds. The isomerases are particularly important in the high fructose corn syrup industry. For example, the aldose-ketose isomerase reaction, catalyzed by glucose isomerase, involves the conversion of glucose to fructose and is just one of three key enzyme reactions in the industry. Sweetzyme ® product is a liquid enzymatic composition containing glucose isomerase which is supplied by Novo Nordisk.

Redox enzymes are enzymes that act as catalysts in chemical oxidation/reduction reactions and, consequently, are involved in the breakdown and synthesis of many biochemicals. Currently, many redox enzymes have not gained a prominent place in industry since most redox enzymes require the presence of a cofactor. However, where cofactors are an integral part of an enzyme or do not have to be supplied, redox enzymes are commercially useful, particularly in the food processing industry.

The redox enzyme, glucose oxidase, is used to prevent unwanted browning reactions affecting food color and flavor. Glucose oxidase is also used as an "oxygen scavenger" to prevent the development of off-flavors in juices and to preserve color and stability in certain sensitive food ingredients. The redox enzyme, catalase, has been utilized to decompose residual hydrogen peroxide used as a sterilizing agent. A third redox enzyme, lipoxidase (lipoxygenase), found naturally in soya flour and not usually purified for industrial use, is used in baking, not only to obtain whiter bread, but also to reverse the dough-softening effects caused by certain agents. Other redox enzymes have possible applications ranging from the enzymatic synthesis of steroid derivatives to use in diagnostic tests. These redox enzymes include peroxidase, superoxide dismutase, alcohol oxidase, polyphenol oxidase, xanthine oxidase, sulfhydryl oxidase, hydroxylases, cholesterol oxidase, laccase, alcohol dehydrogenase, and steroid dehydrogenases.

When enzymes, such as those described above, are prepared or sold for use in industrial processes, they generally are formulated into liquid enzymatic compositions designed for a particular process. These liquid enzymatic compositions, however, have historically been plagued with problems such as chemical instability which can result in the loss of enzymatic activity, particularly upon storage. This critical problem of loss of enzymatic activity due to storage has particularly affected the liquid detergent industry. It is not uncommon to have industrial products, such as liquid enzymatic compositions, stored in warehouses in various climates around the world where the product is subjected to a temperature that may range from freezing to above 50° C. for extended periods. After storage at temperature extremes ranging from 0° C. to 50° C. for many months, most liquid enzymatic compositions lose from 20 to 100 percent of their enzymatic activity due to enzyme instability.

Various attempts have been made to stabilize enzymes contained in liquid enzymatic compositions. Attempts to increase the stability of liquid enzynatic compositions using formulations containing alcohols, glycerols, dialkylglycolethers, and mixtures of these and other compounds have had only marginal success, even in moderate storage temperature ranges.

In U.S. Pat. No. 4,801,544, a system of ethylene glycol and ethoxylated linear alcohol nonionic surfactant with hydrocarbon solvent was utilized as a stabilizer and the encapsulation of enzymes in micelles within the solvent/surfactant mixture was described. However, the water content of the composition was kept at less than 5 percent, and enzyme stability was checked at 35°, 70° and 100° F.

The stabilization of an aqueous enzyme preparation using certain esters has been described in U.S. Pat. No. 4,548,727. The ester used as a stabilizer has the formula, RCOOR', where R is an alkyl of from one to three carbons or hydrogen, and R' is an alkyl of from one to six carbons. The ester is present in the aqueous enzyme preparation in an amount from 0.1 to about 2.5% by weight.

U.S. Pat. No. 4,318,818 describes a stabilizing system for aqueous enzyme compositions where the stabilizing system comprises calcium ions and a low molecular weight carboxylic acid or its salt. The pH of the stabilizing system is from about 6.5 to about 10.

U.S. Pat. No. 4,243,543 teaches the stabilization of liquid proteolytic enzyme-containing detergent compositions. The detergent compositions are stabilized by adding an antioxidant and a hydrophilic polyol to the composition while stabilizing the pH of the composition.

U.S. Pat. No. 4,169,817 teaches a liquid cleaning composition containing stabilized enzymes. The composition is an aqueous solution containing from 10% to 50% by weight of solids and including detergent builders, surface active agents, an enzyme system derived from Bacillus subtilis and an enzyme stabilizing agent. The stabilizing agents comprise highly water soluble sodium or potassium salts and/or water soluble hydroxy alcohols and enable the solution to be stored for extended periods without deactivation of the enzymes.

European Pat. No. 0 352 244 A2 describes stabilized liquid detergent compositions using an amphoteric surfactant.

It is an object of the present invention to provide a formulation capable of stabilizing one or more enzymes contained in a liquid enzymatic composition.

A second object of the invention is to provide a stabilized liquid enzynatic composition.

A third object of the invention is to provide a method for the stabilization of a liquid enzymatic composition.

These objects can be accomplished in part by the use of a stabilizing formulation for a liquid enzymatic composition comprising at least one water-soluble coupling agent selected from a short chain alcohol and a short chain glycol, at least one of (i) a polyethoxylated alkyl diamine and (ii) an amine oxide, and water. The water-soluble coupling agent is present in an amount effective to increase the solubility of the polyethoxylated alkyl diamine and/or the amine oxide in the water, and the at least one of (i) a polyethoxylated alkyl diamine and (ii) an amine oxide are present in an amount effective to stabilize one or more enzymes contained in a liquid enzymatic composition. This stabilizing formulation can be employed with a wide variety of enzymes utilized in liquid enzymatic compositions performing a wide variety of functions. The enzyme classes with which this stabilizing formulation can be used include, but are not limited to, the enzyme classes heretofore discussed.

The invention also relates to a stabilized liquid enzymatic composition comprising at least one water-soluble coupling agent selected from a short chain alcohol and a short chain glycol, at least one of (i) a polyethoxylated alkyl diamine and (ii) an amine oxide, water, and at least one enzyme. The water-soluble coupling agent is present in an amount effective to increase the solubility of the polyethoxylated alkyl diamine and/or the amine oxide in the water, and the at least one of (i) a polyethoxylated alkyl diamine and (ii) an amine oxide are present in an amount effective to stabilize the at least one enzyme contained in the liquid enzymatic composition.

The invention further relates to a method for the stabilization of a liquid enzymatic composition comprising the steps of:

(a) adding to water at least one water-soluble coupling agent selected from a short chain alcohol and a short chain glycol, (b) adding at least one of (i) a polyethoxylated alkyl diamine and (ii) an amine oxide to the water containing said coupling agent resulting from step (a) to form a water-based formulation, and (c) adding at least one enzyme to the water-based formulation resulting from step (b), wherein the coupling agent is present in an amount effective to increase the solubility of the at least one of (i) a polyethoxylated alkyl diamine and (ii) an amine oxide in said water, and further wherein the at least one of (i) a polyethoxylated alkyl diamine and (ii) an amine oxide is present in an amount effective to stabilize the at least one enzyme.

The invention further relates to a method for the stabilization of a liquid enzymatic composition comprising the steps of:

(a) adding to water at least one water-soluble coupling agent selected from a short chain alcohol and a short chain glycol, (b) adding at least one of (i) a polyethoxylated alkyl diamine and (ii) an amine oxide to the water containing the coupling agent resulting from step (a) to form a water-based formulation, and (c) combining the water based formulation with a liquid enzymatic composition containing at least one enzyme, wherein the coupling agent is present in an amount effective to increase the solubility of the at least one of (i) a polyethoxylated alkyl diamine and (ii) an amine oxide in the water, and further wherein the at least one of (i) a polyethoxylated alkyl diamine and (ii) an amine oxide is present in an amount effective to stabilize the at least one enzyme contained in said liquid enzymatic formulation.

The invention further relates to a stabilized liquid enzymatic composition comprising:

(a) a polyethoxylated alkyl diamine, and (b) at least one enzyme, wherein ingredient (a) is present in an amount effective to stabilize the at least one enzyme.

The invention further relates to a stabilized liquid enzymatic composition comprising:

(a) an amine oxide, and (b) at least one enzyme, wherein ingredient (a) is present in an amount effective to stabilize the at least one enzyme.

The invention further relates to a stabilized liquid enzymatic composition comprising:

(a) at least one of (i) a polyethoxylated alkyl diamine and (ii) an amine oxide, and (b) at least one enzyme, wherein ingredient (a) is present in an amount effective to stabilize the at least one enzyme.

The water-soluble coupling agent employed in the present invention is used to increase the solubility of the polyethoxylated alkyl diamine and/or the amine oxide in water and to increase their final concentrations in the stabilizing formulation beyond that which could be achieved in the absence of the coupling agent. When stabilizing a pre-formulated liquid enzymatic composition, however, the water-soluble coupling agent may or may not be needed to solubilize the polyethoxylated alkyl diamine or the amine oxide. These pre-formulated liquid enzymatic compositions include both water-based compositions and those formulated or employed in organic solvents or media.

The water-soluble coupling agent when employed is selected from at least one of a short chain alcohol and a short chain glycol. Preferably, the coupling agent is selected from a $C_1$–$C_6$ alcohol and a $C_2$–$C_6$ glycol, each having a backbone of up to six carbons. Most preferably, the alcohol and glycol are selected from ethanol, propanol, butylene glycol, propylene glycol, and hexylene glycol. When a longer chain polyethoxylated alkyl diamine is used in the stabilizing formulation, a smaller chain polyethoxylated alkyl diamine can act as a coupling agent for the longer chain polyethoxylated alkyl diamine.

The stabilizing formulation also contains at least one of (i) a polyethoxylated alkyl diamine and (ii) an amine oxide. Depending on the enzyme to be stabilized, the stabilizing formulation may contain either (i) at least one polyethoxylated alkyl diamine or (ii) at least one amine oxide, or a combination of (i) and (ii). For example, a polyethoxylated alkyl diamine may be used in conjunction with the above coupling agent to the exclusion of an amine oxide. Alternatively, an amine oxide may be used in conjunction with a coupling agent to the exclusion of a polyethoxylated alkyl diamine. Most preferably, a combination of both (i) and (ii) are used in the stabilizing formulation. One skilled in the art can readily and routinely determine an appropriate combination for a specific liquid enzyme composition to be stabilized.

Preferably, the polyethoxylated alkyl diamine useful to practice the invention includes a compound of the formula:

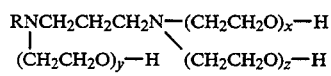

wherein the sum of x, y, and z is from 2 to 20, and R is a $C_3$–$C_{22}$ alkyl. The polyethoxylated alkyl diamine is generally available as a mixture of compounds, or "cuts," representing the degree of ethoxylation, and having common characteristics such as the alkyl portion and molecular weights ranging from 220 to 515. The most preferred polyethoxylated alkyl diamines are: N,N,N-tris(2- hydroxyethyl)-N-tallow-1,3 diaminopropane, N,N,N-polyoxyethylene(10)-N-tallow-1,3 diaminopropane, N,N,N-polyoxyethylene(13)-N-tallow-1,3 diaminopropane, N,N,N-polyoxyethylene(15)-N-tallow-1,3 diaminopropane, N,N,N-polyoxyethylene(20)-N-tallow-1,3 diaminopropane, and N,N,N-polyoxyethylene(25)-N-tallow-1,3 diaminopropane. Polyethoxylated alkyl diamines can be obtained from a commercial source such as Akzo Chemical Division of McCook, Ill. These products are sold under the tradename, Ethoduomeen.

The stabilizing formulation of this invention may contain an amine oxide. Preferably, the amine oxide employed is a tertiary amine oxide of the formula:

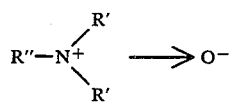

wherein R' is methyl, hydroxymethyl, ethyl, or hydroxyethyl, and R" is a $C_8$–$C_{22}$ alkyl. Particularly preferred amine oxides are: Bis(2 hydroxyethyl) cocoamine oxide, Bis(2 hydroxyethyl) tallowamine oxide, Dimethyl cocoamine oxide, Dimethyl tallowamine oxide, and Dimethyl hexadecylamine oxide. Amine oxides can be obtained from a number of commercial sources such as Akzo Chemicals, Inc., Sherex Chemicals, Stepan, Lonza, Proctor & Gamble, and Jordon Chemical Co. The amine oxide products available from Akzo Chemicals, Inc. are sold under the tradename, Aromox.

The stabilizing formulation described here can be employed with a wide variety of enzymes and industrial processes or products. The enzyme, industrial processes and industrial products with which this stabilizing formulation can be used include, but are not limited to, those heretofore discussed.

The use of the stabilizing formulation to stabilize an enzyme composition results in a second embodiment of this invention, a stabilized liquid enzymatic composition. Thus, the invention also relates to a stabilized liquid enzymatic composition comprising at least one water-soluble coupling agent selected from a short chain alcohol and a short chain glycol, at least one of (i) a polyethoxylated alkyl diamine and (ii) an amine oxide, water, and an enzyme.

The contemplated and preferred embodiments regarding the water soluble coupling agent, polyethoxylated alkyl diamine, and amine oxide present in this stabilized liquid enzymatic composition are the same as those discussed above with respect to the stabilizing formulation of this invention.

As with the stabilizing formulation, the liquid enzymatic composition of this invention can be practiced with a wide variety of enzymes. These enzymes include, but are not limited to, the enzyme classes and specific enzymes heretofore discussed. Enzymes that may be used are derived from animal, plant, fungal, bacterial, and synthetic sources. Preferred enzymes are proteases, including acid, alkaline, and neutral proteases, which are widely used in the laundry detergent and cheese making industries; amylases, including acid, alkaline, and neutral amylases, used, for example, in the corn syrup industry; and lipases, used in developing flavors in cheese, and in the pulp and paper and leather making industries.

In the stabilized liquid enzyme composition of the invention, the coupling agent may preferably be present from 0.1 to 30% by weight of the composition, but more preferably from 1 to 20%. The polyethoxylated alkyl diamine, if present, may preferably be present from 0.1 to 50% by weight of the composition, but more preferably from 1 to 30%.

The amine oxide, if present, may also preferably be present from 0.1 to 50% by weight of the composition, but more preferably from 1 to 30%. The amount of water present may preferably vary from 10 to 80% by weight of the composition.

The amount of enzyme present in the form of a dilution of the concentrated enzyme may preferably range from 0.001 to 50% by weight of the concentrated composition, but more preferably from 0.01 to 25% by weight. The amount of enzyme present, however, is highly dependent upon the activity of the enzyme and the desired end use.

Depending upon the enzyme it contains and its intended use, the pH of the final stabilized liquid enzymatic composition preferably varies from 4.0 to 11.0, but more preferably from 5.0 to 10.0. As understood in the art, adjustment of pH may be necessary with a small amount of acid or alkaline material.

The stabilized liquid enzymatic composition may contain other additives directed toward the use of the composition in a particular industrial process. For example, the stabilized liquid enzymatic composition can contain additives such as surfactants, defoamers, and the like, as are known in the art. Advantageously, when a stabilized liquid enzymatic composition of the invention is used, the stabilizing formulation may also act as a dispersant aid for the enzyme in industrial process waters.

The present invention also relates to a method for the stabilization of a liquid enzymatic composition comprising the steps described above. Illustrative and preferred components, as well as the amounts of the components used in the steps, are the same as discussed above.

One of ordinary skill would understand that the components of the stabilized liquid enzymatic composition can be combined in any order or even simultaneously. However, the order of (a) adding to water at least one water-soluble coupling agent selected from a short chain alcohol and a short chain glycol, (b) adding at least one of (i) a polyethoxylated alkyl diamine and (ii) an amine oxide to the water containing the coupling agent resulting from step (a) to form a water-based formulation, and (c) adding at least one enzyme to the water-based formulation of step (b) is preferred. When other additives are to be included in the stabilized liquid enzymatic composition, such additives may be added at any time, but preferably after the coupling step, or in a separate step from the step in which the enzyme is added.

One of ordinary skill would also recognize that the coupling step and the addition of at least one of (i) a polyethoxylated alkyl diamine and (ii) an amine oxide to the coupled water resulting from the coupling step result in a stabilizing formulation according to the embodiment of the invention discussed above. These steps can be performed in any order or even simultaneously, but the order set out above is preferred.

An alternative method for the stabilization of a liquid enzymatic composition comprises the steps of (a) adding to water at least one water-soluble coupling agent selected from a short chain alcohol and a short chain glycol, (b) adding at least one of (i) a polyethoxylated alkyl diamine and (ii) an amine oxide to the water containing the coupling agent resulting from step (a) to form a water-based formulation, and (c) combining the water based formulation with a liquid enzymatic composition containing at least one enzyme.

The following examples are given to illustrate the invention. It should be understood, however, that the invention is not to be limited to the specific conditions or details set forth in these examples.

Example 1

Stabilized liquid enzymatic compositions were prepared according to the invention. The amount of each component is expressed as % by weight of the total composition and is set forth in Table 1. The order of addition of the components was the preferred order described above. Table 2 sets forth, with their related codes, various nonstabilized native liquid enzymatic concentrates and their dilutions with 95% water. These nonstablized concentrates were used in the preparation of the stabilized liquid enzymatic compositions in Tables 1 and 3.

TABLE 1

| STABILIZED ENZYMATIC COMPOSITIONS | | | | |
|---|---|---|---|---|
| | A | B | C | D |
| HT-Proteolytic ® (enzyme) | 10 | 0 | 0 | 0 |
| Diazyme L-200 ® (enzyme) | 0 | 10 | 0 | 0 |
| Lipolase ® 100 (enzyme) | 0 | 0 | 5 | 0 |
| Lipase (enzyme) | 0 | 0 | 0 | 5 |
| Amine Oxide[1/] | 1 | 20 | 10 | 10 |
| Polyethoxylated alkyl diamine[2/] | 15 | 2 | 1 | 1 |
| Hexylene Glycol | 10 | 10 | 5 | 5 |
| Ethanol | 10 | 5 | 2 | 2 |
| Water | 54 | 53 | 77 | 77 |

[1/]Aromox C-12 product, bis 2-hydroxyethyl cocoamine oxide, available from Akzo Chemicals, Inc.
[2/]Ethoduomeen T-13 product, 13-ethoxylate, tallow alkyl (N,N,N-polyoxyethylene(13)-N-tallow-1,3 diaminopropane), available from Akzo Chemicals, Inc.

TABLE 2

| ENZYMATIC COMPOSITIONS | | |
|---|---|---|
| | 100% Concentrate | 95% Aqueous Dilution |
| HT-Proteolytic ® | Aa | Aa1 |
| Diazyme L-200 ® | Bb | Bb1 |
| Lipolase ® 100 | Cc | Cc1 |
| Lipase | Dd | Dd1 |

Example 2

The enzymatic stability of the stabilized liquid enzymatic compositions was compared with that of the enzymatic concentrates and aqueous dilutions at 50° C. The results, presented in Table 3, indicate 95% or greater stability after 12 weeks at 50° C. for the stabilized liquid enzymatic compositions, whereas the native enzymatic concentrates and aqueous dilutions showed significant loss of enzyme activity after 2 weeks at 50° C.

TABLE 3

| ENZYMATIC STABILITY AT 50° C. | | | | | |
|---|---|---|---|---|---|
| | % Activity Present | | | | |
| | | After Week No. | | | |
| Formulas | Initial | 2 | 4 | 8 | 12 |
| A | 100 | 100 | 100 | 100 | 100 |
| Aa | 100 | 27 | 0 | 0 | 0 |
| Aa1 | 100 | 16 | 0 | 0 | 0 |
| B | 100 | 100 | 100 | 100 | 96 |
| Bb | 100 | 33 | 0 | 0 | 0 |
| Bb1 | 100 | 24 | 0 | 0 | 0 |
| C | 100 | 100 | 100 | 98 | 95 |
| Cc | 100 | 49 | 4 | 0 | 0 |
| Cc1 | 100 | 21 | 0 | 0 | 0 |
| D | 100 | 100 | 100 | 95 | 95 |
| Dd | 100 | 54 | 7 | 0 | 0 |
| Dd1 | 100 | 36 | 3 | 0 | 0 |

Example 3

The stabilized liquid enzymatic compositions, enzymatic concentrates, and aqueous dilutions were all subjected to freeze/thaw cycles followed by assay of % enzymatic activity remaining after each cycle. The stabilized liquid enzymatic compositions displayed greater than 90% activity remaining even after six cycles were performed. Further, it was observed that even one freeze/thaw cycle significantly inactivated the concentrates and simple aqueous dilutions of these concentrates. The results are presented in Table 4.

TABLE 4

% ACTIVITY AFTER FREEZE/THAW CYCLE

| Formulas | Initial | Freeze/Thaw Cycle # | | | | | |
|---|---|---|---|---|---|---|---|
| | | 1 | 2 | 3 | 4 | 5 | 6 |
| A | 100 | 100 | 100 | 100 | 100 | 100 | 100 |
| Aa | 100 | 56 | 0 | 0 | 0 | 0 | 0 |
| Aa1 | 100 | 11 | 0 | 0 | 0 | 0 | 0 |
| B | 100 | 100 | 100 | 100 | 100 | 100 | 94 |
| Bb | 100 | 73 | 18 | 0 | 0 | 0 | 0 |
| Bb1 | 100 | 14 | 0 | 0 | 0 | 0 | 0 |
| C | 100 | 100 | 100 | 100 | 100 | 98 | 93 |
| Cc | 100 | 28 | 0 | 0 | 0 | 0 | 0 |
| Cc1 | 100 | 5 | 0 | 0 | 0 | 0 | 0 |
| D | 100 | 100 | 100 | 100 | 100 | 95 | 91 |
| Dd | 100 | 15 | 0 | 0 | 0 | 0 | 0 |
| Dd1 | 100 | 3 | 0 | 0 | 0 | 0 | 0 |

The claimed invention is:

1. A formulation for stabilizing a liquid enzymatic composition consisting essentially of:
   (a) at least one water-soluble coupling agent selected from a short carbon chain alcohol and a short carbon chain glycol,
   (b) at least one of (i) a polyethoxylated alkyl diamine and
   (ii) an amine oxide, and
   (c) water wherein ingredient (a) is present in an amount effective to increase the solubility of ingredient (b) in said water, and said ingredient (b) is present in an amount effective to stabilize one or more enzymes contained in a liquid enzymatic composition.

2. The stabilizing formulation of claim 1 wherein said polyethoxylated alkyl diamine is at least one compound of the formula:

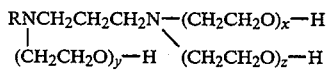

wherein the sum of x, y, and z is from 2 to 20, and
R is a $C_3$–$C_{22}$ alkyl radical.

3. The stabilizing formulation of claim 2 wherein said polyethoxylated alkyl diamine is at least one compound selected from N,N,N-tris(2-hydroxyethyl)-N-tallow-1,3 diaminopropane, N,N,N-polyoxyethylene(10)-N-tallow-1,3 diaminopropane, and N,N,N-polyoxyethylene(15)-N-tallow-1,3 diaminopropane.

4. The stabilizing formulation of claim 1 wherein said amine oxide is at least one tertiary amine oxide of the formula

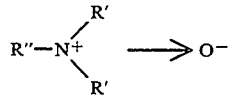

wherein R′ is methyl, hydroxymethyl, ethyl, or hydroxyethyl, and R″ is a $C_8$–$C_{22}$ alkyl radical.

5. The stabilizing formulation of claim 4 wherein said amine oxide is at least one compound selected from bis(2-hydroxyethyl) cocoamine oxide, bis(2-hydroxyethyl) tallowamine oxide, dimethyl cocoamine oxide, dimethyl tallowamine oxide, and dimethyl hexadecylamine oxide.

6. The stabilizing formulation of claim 1, wherein said coupling agent is selected from a $C_1$–$C_6$ alcohol and a $C_2$–$C_6$ glycol.

7. The stabilizing formulation of claim 6, wherein said coupling agent is selected from ethanol, propanol, butylene glycol, propylene glycol, and hexylene glycol.

8. A stabilized liquid enzymatic composition consisting essentially of:
   (a) at least one water-soluble coupling agent selected from a short carbon chain alcohol and a short carbon chain glycol,
   (b) at least one of (i) a polyethoxylated alkyl diamine and
   (ii) an amine oxide,
   (c) water, and
   (d) at least one enzyme wherein ingredient (a) is present in an amount effective to increase the solubility of ingredient (b) in said water, and said ingredient (b) is present in an amount effective to stabilize said enzyme.

9. The composition of claim 8 wherein said polyethoxylated alkyl diamine is at least one compound of the formula:

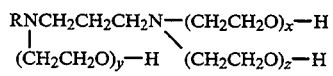

wherein the sum of x, y, and z is from 2 to 20, and
R is a $C_3$–$C_{22}$ alkyl radical.

10. The composition of claim 9 wherein said polyethoxylated alkyl diamine is at least one compound selected from N,N,N-tris(2 hydroxyethyl)-N-tallow-1,3 diaminopropane, N,N,N-polyoxyethylene(10)-N-tallow-1,3 diaminopropane, and N,N,N-polyoxyethylene(15)-N-tallow-1,3 diaminopropane 11. The composition of claim 8 wherein said amine oxide is at least one tertiary amine oxide of the formula

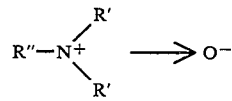

wherein R′ is methyl, hydroxymethyl, ethyl, or hydroxyethyl, and R″ is a $C_8$–$C_{22}$ alkyl radical.

12. The composition of claim 1 wherein said amine oxide is at least one compound selected from bis(2-hydroxyethyl) cocoamine oxide, bis(2-hydroxyethyl) tallowamine oxide, dimethyl cocoamine oxide, dimethyl tallowamine oxide, and dimethyl hexadecylamine oxide.

13. The composition of claim 8, wherein said coupling agent is selected from a $C_1$–$C_6$ alcohol and a $C_2$–$C_6$ glycol.

14. The composition of claim 13, wherein said coupling agent is selected from ethanol, propanol, butylene glycol, propylene glycol, and hexylene glycol.

15. The composition of claim 8, wherein said enzyme is selected from a protease, amylase, and lipase.

16. The composition of claim 8 wherein said-coupling agent is present from 0.1 to 30% by weight of the composition, said polyethoxylated alkyl diamine is present from 0.1 to 50% by weight of the composition, and said amine oxide is present from 0.1 to 50% by weight of the composition.

17. A method for the preparation of a stabilized liquid enzymatic composition consisting essentially of the steps of:
   (a) adding to water at least one water-soluble coupling agent selected from a short carbon chain alcohol and a short carbon chain glycol,
   (b) adding at least one of (i) a polyethoxylated alkyl diamine and (ii) an amine oxide to the water containing said coupling agent resulting from step (a) to form a water-based formulation, and
   (c) adding at least one enzyme to the water-based formulation resulting from step (b), wherein said coupling agent is present in an amount effective to increase the solubility of said at least one of (i) a polyethoxylated alkyl diamine and (ii) an amine oxide in said water, and further wherein said at least one of (i) a polyethoxylated alkyl diamine and (ii) an amine oxide is present in an amount effective to stabilize said at least one enzyme.

18. The method of claim 17 wherein said polyethoxylated alkyl diamine is at least one compound of the formula:

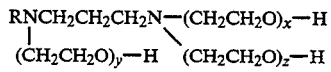

wherein the sum of x, y, and z is from 2 to 20, and
R is a $C_3$–$C_{22}$ alkyl radical.

19. The method of claim 18 wherein said polyethoxylated alkyl diamine is at least one compound selected from N,N,N-tris(2-hydroxyethyl)-N-tallow-1,3 diaminopropane, N,N,N-polyoxyethylene(10)-N-tallow-1,3 diaminopropane, and N,N,N-polyoxyethylene(15)-N-tallow-1,3 diaminopropane.

20. The method of claim 17 wherein said amine oxide is at least one tertiary amine oxide of the formula

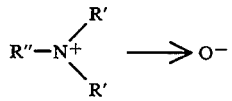

wherein R' is methyl, hydroxymethyl, ethyl, or hydroxyethyl, and R" is a $C_{10}$–$C_{22}$ alkyl radical.

21. The method of claim 20 wherein said amine oxide is at least one compound selected from bis(2-hydroxyethyl) cocoamine oxide, bis(2-hydroxyethyl) tallowamine oxide, dimethyl cocoamine oxide, dimethyl tallowamine oxide, and dimethyl hexadecylamine oxide.

22. The method of claim 17, wherein said coupling agent is selected from a $C_1$–$C_6$ alcohol and a $C_2$–$C_6$ glycol.

23. The method of claim 22, wherein said coupling agent is selected from ethanol, propanol, butylene glycol, propylene glycol, and hexylene glycol.

24. The method of claim 17, wherein said enzyme is selected from a protease, amylase, and lipase.

25. A method for the stabilization of a liquid enzymatic composition consisting essentially of the steps of:
   (a) adding to water at least one water-soluble coupling agent selected from a short carbon chain alcohol and a short carbon chain glycol,
   (b) adding at least one of (i) a polyethoxylated alkyl diamine and (ii) an amine oxide to the water containing said coupling agent resulting from step (a) to form a water-based formulation, and
   (c) combining said water based formulation with a liquid enzymatic composition containing at least one enzyme, wherein said coupling agent is present in an amount effective to increase the solubility of said at least one of (i) a polyethoxylated alkyl diamine and (ii) an amine oxide in said water, and further wherein said at least one of (i) a polyethoxylated alkyl diamine and (ii) an amine oxide is present in an amount effective to stabilize said at least one enzyme contained in said liquid enzymatic formulation.

26. The method of claim 25 wherein said polyethoxylated alkyl diamine is at least one compound of the formula:

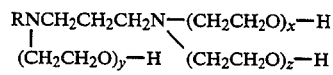

wherein the sum of x, y, and z is from 2 to 20, and
R is a $C_3$–$C_{22}$ alkyl radical.

27. The method of claim 26 wherein said polyethoxylated alkyl diamine is at least one compound selected from N,N,N-tris(2-hydroxyethyl)-N-tallow-1,3 diaminopropane, N,N,N-polyoxyethylene(10)-N-tallow-1,3 diaminopropane, and N,N,N-polyoxyethylene(15)-N-tallow-1,3 diaminopropane.

28. The method of claim 25 wherein said amine oxide is at least one tertiary amine oxide of the formula

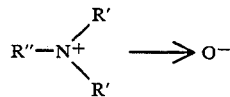

wherein R' is methyl, hydroxymethyl, ethyl, or hydroxyethyl, and R" is a $C_{10}$–$C_{22}$ alkyl radical.

29. The method of claim 28 wherein said amine oxide is at least one compound selected from bis(2-hydroxyethyl) cocoamine oxide, bis(2-hydroxyethyl) tallowamine oxide, dimethyl cocoamine oxide, dimethyl tallowamine oxide, and dimethyl hexadecylamine oxide.

30. The method of claim 25, wherein said coupling agent is selected from a $C_1$–$C_6$ alcohol and a $C_2$–$C_6$ glycol.

31. The method of claim 30, wherein said coupling agent is selected from ethanol, propanol, butylene glycol, propylene glycol, and hexylene glycol.

32. The method of claim 25, wherein said enzyme is selected from a protease, amylase, and lipase.

33. A stabilized liquid enzymatic composition consisting essentially of:
   (a) a polyethoxylated alkyl diamine, and
   (b) at least one enzyme wherein ingredient (a) is present in an amount effective to stabilize said at least one enzyme.

34. The composition of claim 33, further comprising water.

35. A stabilized liquid enzymatic composition consisting essentially of:
   (a) an amine oxide, and
   (b) at least one enzyme wherein ingredient (a) is present in an amount effective to stabilize said at least one enzyme.

36. The composition of claim 35, further comprising water.

37. A stabilized liquid enzymatic composition consisting essentially of:

(a) at least one of (i) a polyethoxylated alkyl diamine and (ii) an amine oxide, and (b) at least one enzyme wherein ingredient (a) is present in an amount effective to stabilize said at least one enzyme.

38. The composition of claim 37, further comprising water.

39. The composition of claim 37 consisting essentially of:

(a) (i) a polyethoxylated alkyl diamine, (ii) an amine oxide, and (b) an enzyme, wherein ingredient (a) is present in an amount effective to stabilize said enzyme.

40. The composition of claim 39, wherein:

said polyethoxylated alkyl diamine is selected from N,N,N-tris(2-hydroxyethyl)-N-tallow-1,3-diaminopropane, N,N,N-polyoxyethylene(10)-N-tallow-1,3diaminopropane, and N,N,N-polyoxyethylene(15)-N-tallow-1,3 diaminopropane, said amine oxide is selected from bis (2-hydroxyethyl) cocoamine oxide, bis(2-hydroxyethyl) tallowamine oxide, dimethyl cocoamine oxide, dimethyl tallowamine oxide, and dimethyl hexadecylamine oxide, and said enzyme is selected from a protease, an amylase and a lipase.

41. The method of claim 25 consisting essentially of the steps of:

(a) adding to water at least one water-soluble coupling agent selected from a short carbon chain alcohol and a short carbon chain glycol, (b) adding a polyethoxylated alkyl diamine and an amine oxide to the water containing said coupling agent resulting from step (a) to form a water-based formulation, and (c) combining said water based formulation with a liquid enzymatic composition containing an enzyme, wherein said coupling agent is present in an amount effective to increase the solubility of said polyethoxylated alkyl diamine and said amine oxide in said water, and further wherein said polyethoxylated alkyl diamine and said amine oxide are present in a combined amount effective to stabilize said enzyme contained in said liquid enzymatic formulation.

42. The method of claim 41, wherein:

said water-soluble coupling agent is selected from ethanol, propanol, butylene glycol, propylene glycol, and hexylene glycol, said polyethoxylated alkyl diamine is selected from N,N,N-tris(2-hydroxyethyl)-N-tallow-1,3 diaminopropane, and N,N,N-polyoxyethylene(10)-N-tallow-1,3 diaminopropane, and N,N,N-polyoxyethylene(15)-N-tallow-1,3 diaminopropane, and said amine oxide is selected from bis(2-hydroxyethyl) cocoamine oxide, bis(2-hydroxyethyl) tallowamine oxide, dimethyl cocoamine oxide, dimethyl tallowamine oxide, and dimethyl hexadecylamine oxide.

43. The method of claim 17 consisting essentially of the steps of:

(a) adding to water at least one water-soluble coupling agent selected from a short carbon chain alcohol and a short carbon chain glycol, (b) adding a polyethoxylated alkyl diamine and an amine oxide to the water containing said coupling agent resulting from step (a) to form a water-based formulation, and (c) adding an enzyme to the water-based formulation resulting from step (b), wherein said coupling agent is present in an amount effective to increase the solubility of said polyethoxylated alkyl diamine and said amine oxide in said water, and further wherein said polyethoxylated alkyl diamine and said amine oxide are present in a combined amount effective to stabilize said enzyme.

44. The method of claim 43, wherein:

said water-soluble coupling agent is selected from ethanol, propanol, butylene glycol, propylene glycol, and hexylene glycol, said polyethoxylated alkyl diamine is selected from N,N,N-tris(2-hydroxyethyl)-N-tallow-1,3 diaminopropane, N,N,N-polyoxyethylene(10)-N-tallow-1,3 diaminopropane, and N,N,N-polyoxyethylene(15)-N-tallow-1,3 diaminopropane, and said amine oxide is selected from bis(2-hydroxyethyl) cocoamine oxide, bis(2-hydroxyethyl) tallowamine oxide, dimethyl cocoamine oxide, dimethyl tallowamine oxide, and dimethyl hexadecylamine oxide.

45. The composition of claim 8 consisting essentially of:

(a) a water-soluble coupling agent selected from a short carbon chain alcohol and a short carbon chain glycol, (b) (i) a polyethoxylated alkyl diamine, (ii) an amine oxide, (c) water, and (d) an enzyme wherein ingredient (a) is present in an amount effective to increase the solubility of ingredient (b) in said water, and wherein ingredient (b) is present in an amount effective to stabilize said enzyme.

46. The composition of claim 45, wherein:

said water-soluble coupling agent is selected from ethanol, propanol, butylene glycol, propylene glycol, and hexylene glycol, said polyethoxylated alkyl diamine is selected from N,N,N-tris(2-hydroxyethyl)-N-tallow-1,3 diaminopropane, N,N,N-polyoxyethylene(10)-N-tallow-1,3 diaminopropane, and N,N,N-polyoxyethylene(15)-N-tallow-1,3 diaminopropane, said amine oxide is selected from bis(2-hydroxyethyl) cocoamine oxide, bis(2-hydroxyethyl) tallowamine oxide, dimethyl cocoamine oxide, dimethyl tallowamine oxide, and dimethyl hexadecylamine oxide, and said enzyme is selected from a protease, an amylase, and a lipase.

47. The stabilizing formulation of claim 1 consisting essentially of:

(a) a water-soluble coupling agent selected from a short carbon chain alcohol and a short carbon chain glycol, (b) (i) a polyethoxylated alkyl diamine, (ii) an amine oxide, and (c) water wherein ingredient (a) is present in an amount effective to increase the solubility of ingredient (b) in said water, and wherein ingredient (b) is present in an amount effective to stabilize an enzyme contained in a liquid enzymatic composition.

48. The stabilizing formulation of claim 47, wherein:

said water-soluble coupling agent is selected from ethanol, propanol, butylene glycol, propylene glycol, and hexylene glycol, said polyethoxylated alkyl diamine is selected from N,N,N-tris(2-hydroxyethyl)-N-tallow-1,3 diaminopropane, N,N,N-polyoxyethylene(10)-N-tallow-1,3 diaminopropane, and N,N,N-polyoxyethylene(15)-N-tallow-1,3 diaminopropane, and said amine oxide is selected from bis(2-hydroxyethyl) cocoamine oxide, bis(2-hydroxyethyl) tallowamine oxide, dimethyl cocoamine oxide, dimethyl tallowamine oxide, and dimethyl hexadecylamine oxide.

49. The stabilizing formulation of claim 47, wherein:
said water-soluble coupling agent is ethanol, hexylene glycol or a mixture thereof,
said polyethoxylated alkyl diamine is tallow alkyl (N,N,N-polyoxyethylene (13)-N-tallow-1,3 diaminopropane), and
said amine oxide is bis 2-hydroxyethyl cocoamine oxide.

* * * * *

UNITED STATES PATENT AND TRADEMARK OFFICE
CERTIFICATE OF CORRECTION

PATENT NO. : 5,356,800
DATED : October 18, 1994
INVENTOR(S) : Percy A. JAQUESS

It is certified that error appears in the above-indentified patent and that said Letters Patent is hereby corrected as shown below:

Claim 40, col. 15, line 18, delete "1,3diaminopropane" and insert therefor --1,3 diaminopropane--.

Claim 44, col. 16, line 20, delete "cocamine" and insert therefor --cocoamine--.

Signed and Sealed this

Fourteenth Day of March, 1995

Attest:

BRUCE LEHMAN

*Attesting Officer*   *Commissioner of Patents and Trademarks*